(12) United States Patent
Bales, Jr. et al.

(10) Patent No.: US 6,449,834 B1
(45) Date of Patent: Sep. 17, 2002

(54) ELECTRICAL CONDUCTOR COILS AND METHODS OF MAKING SAME

(75) Inventors: Thomas O. Bales, Jr.; Francisco Avellanet, both of Coral Gables, FL (US)

(73) Assignee: Scilogy Corp., Miami, FL (US)

( * ) Notice: Subject to any disclaimer, the term of this patent is extended or adjusted under 35 U.S.C. 154(b) by 0 days.

(21) Appl. No.: 09/048,775

(22) Filed: Mar. 26, 1998

Related U.S. Application Data

(63) Continuation-in-part of application No. 08/843,405, filed on May 2, 1997, now Pat. No. 5,994,647, and a continuation-in-part of application No. 08/963,686, filed on Nov. 4, 1997, now Pat. No. 6,049,042.

(51) Int. Cl.⁷ .............................................. H01R 43/00
(52) U.S. Cl. ........................ 29/825; 29/828; 29/868; 29/745; 228/173.5
(58) Field of Search ..................... 29/828, 868, 872, 29/825, 745, 819, 605; 228/257, 173.5

(56) References Cited

U.S. PATENT DOCUMENTS

| | | | |
|---|---|---|---|
| 251,114 A | 12/1881 | Hallidie | |
| 300,741 A | * 6/1884 | Spruce | 72/64 |
| 1,742,172 A | 12/1929 | Atwood | |
| 1,888,076 A | 11/1932 | Evans | |
| 1,888,807 A | 11/1932 | Rivers | |
| 1,904,162 A | 4/1933 | Milliken | |
| 1,943,082 A | 1/1934 | MacKenzie | 261/49 |
| 1,943,086 A | * 1/1934 | McKnight | 173/264 |
| 1,943,087 A | 1/1934 | Potter | 173/264 |
| 2,071,709 A | 2/1937 | Riddle | 117/16 |
| 2,135,800 A | 11/1938 | Davignon | 88/52 |
| 2,154,551 A | 4/1939 | Wodtke | 174/128 |
| 2,156,652 A | 5/1939 | Harris | 57/145 |
| 2,250,610 A | * 7/1941 | Simons | 29/33 |
| 2,396,734 A | 3/1946 | Williams, Jr. | 174/128 |
| 2,427,507 A | 9/1947 | Powell, 3rd et al. | 57/164 |
| 2,978,860 A | 4/1961 | Campbell | 57/148 |
| 3,038,592 A | * 7/1962 | Kelday et al. | 205/29 |
| 3,083,817 A | 4/1963 | Campbell | 205/2 |
| 3,130,536 A | 4/1964 | Peterson et al. | 57/161 |
| 3,131,469 A | * 5/1964 | Glaze | 29/470.5 |
| 3,158,258 A | * 11/1964 | Kelday et al. | 205/15 |
| 3,195,299 A | 7/1965 | Dietz | 57/149 |

(List continued on next page.)

FOREIGN PATENT DOCUMENTS

| | | |
|---|---|---|
| DE | 595245 | 3/1934 |
| EP | 0480427 A1 | 4/1992 |
| EP | 0 537 618 A1 | 4/1993 |
| EP | 0642 876 A1 | 3/1995 |
| EP | 0649636 A3 | 4/1995 |
| EP | 0649636 A2 | 4/1995 |
| EP | 0666086 A1 | 8/1995 |
| GB | 278233 | 10/1927 |
| GB | 197692 | * 5/1999 |

OTHER PUBLICATIONS

Suhner, How to produce efficiently flexible shafts and casings; May/Jun. 1978, Wire, pp. 109–112.

W.Berg, More twists for flexible shafts couplings; Aug. 21, 1997, Machine Design, p. 152.

Fogiel, Modern Microelectronics, 1972, pp. 735–737.

Kelly, A Plating Process for Ensuring Component Lead Solderability, SMT, Oct. 1997, pp. 68,70.

Reducing Restenosis with Endovascular Brachytherapy, Medpro Month, Jan. 1998, vol. VIII, No. 1

*Primary Examiner*—Lee Young
*Assistant Examiner*—Rick Kiltae Chang
(74) *Attorney, Agent, or Firm*—Patrick J. Walsh

(57) ABSTRACT

Methods of making electrical conductors by twisting a plurality of strands to form a bundle, winding the bundle to form a coil, fusing some of the strands together, optionally drawing the bundle prior to winding and fusing utilising materials and coatings disclosed.

8 Claims, 3 Drawing Sheets

U.S. PATENT DOCUMENTS

| | | | |
|---|---|---|---|
| 3,234,722 A | | 2/1966 | Gilmore ..................... 57/145 |
| 3,261,908 A | | 7/1966 | Roche et al. ............... 174/128 |
| 3,295,310 A | | 1/1967 | Beighley ..................... 57/145 |
| 3,352,098 A | | 11/1967 | Gilmore ..................... 57/147 |
| 3,383,704 A | | 5/1968 | Schoerner et al. ........... 57/145 |
| 3,395,528 A | | 8/1968 | Lucht et al. ................. 57/145 |
| 3,444,684 A | | 5/1969 | Schoerner et al. ........... 57/161 |
| 3,601,970 A | | 8/1971 | Roberts et al. .............. 57/153 |
| 3,622,685 A | * | 11/1971 | Crowl ........................ 174/84 |
| 3,693,250 A | * | 9/1972 | Brorein et al. ............... 29/624 |
| 3,699,768 A | | 10/1972 | Roberts et al. .............. 57/144 |
| 3,708,706 A | * | 1/1973 | Akiyama et al. ........... 310/216 |
| 3,791,027 A | * | 2/1974 | Angelo et al. ............... 29/495 |
| 3,812,666 A | | 5/1974 | Sarracino .................. 57/58.52 |
| 3,822,542 A | | 7/1974 | Naud et al. ................... 57/145 |
| 3,831,370 A | | 8/1974 | Gilmore ..................... 57/145 |
| 3,842,185 A | | 10/1974 | Raw et al. ................ 174/23 R |
| 3,883,278 A | | 5/1975 | Hass ......................... 425/135 |
| 3,883,371 A | | 5/1975 | Geary ......................... 148/32 |
| 3,900,347 A | | 8/1975 | Lorenzetti et al. ........ 148/12 B |
| 3,922,841 A | | 12/1975 | Katsumata et al. ........... 57/145 |
| 3,923,003 A | | 12/1975 | Carden ....................... 118/405 |
| 3,934,446 A | | 1/1976 | Avitzur ........................ 72/206 |
| 3,942,309 A | | 3/1976 | Cahill ............................ 57/9 |
| 3,955,390 A | | 5/1976 | Geary ........................... 72/64 |
| 3,961,417 A | * | 6/1976 | George ........................ 29/605 |
| 3,961,514 A | | 6/1976 | Geary ......................... 72/274 |
| 3,972,304 A | | 8/1976 | Boucher ...................... 118/44 |
| 3,990,874 A | | 11/1976 | Schulman ................... 65/4 B |
| 4,020,829 A | | 5/1977 | Willson et al. ............. 128/2 M |
| 4,079,510 A | | 3/1978 | McGrath et al. | 
| 4,109,375 A | * | 8/1978 | Lin et al. ..................... 29/605 |
| 4,125,741 A | | 11/1978 | Wahl et al. ................. 174/120 |
| 4,133,167 A | | 1/1979 | Schofield ....................... 57/12 |
| 4,173,235 A | | 11/1979 | Tipper ......................... 140/82 |
| 4,201,250 A | | 5/1980 | Walling et al. .............. 141/250 |
| 4,212,151 A | | 7/1980 | Schauffele et al. .............. 57/9 |
| 4,215,703 A | | 8/1980 | Willson ...................... 128/772 |
| 4,311,001 A | | 1/1982 | Glushko et al. .............. 57/215 |
| 4,328,662 A | | 5/1982 | Bretegnier et al. ........ 57/58.61 |
| 4,330,956 A | * | 5/1982 | McCarthy ........................ 43/4 |
| 4,349,694 A | | 9/1982 | Vives ..................... 174/128 R |
| 4,352,697 A | * | 10/1982 | Adams et al. ................. 148/2 |
| 4,354,880 A | * | 10/1982 | Adams et al. ................. 148/2 |
| 4,406,058 A | * | 9/1983 | Dixon ......................... 29/809 |
| 4,407,062 A | * | 10/1983 | Sutcliffe et al. .............. 29/599 |
| 4,456,491 A | * | 6/1984 | Adams et al. ................. 148/2 |
| 4,471,527 A | * | 9/1984 | Nishijima .................... 29/872 |
| 4,473,995 A | * | 10/1984 | Gentry ............................ 57/9 |
| 4,514,058 A | | 4/1985 | Walton .................... 350/96.23 |
| 4,525,598 A | * | 6/1985 | Tsukamoto et al. ......... 174/128 |
| 4,529,837 A | * | 7/1985 | Borden ....................... 174/128 |
| 4,534,363 A | | 8/1985 | Gold ........................... 128/772 |
| 4,548,206 A | | 10/1985 | Osborne ..................... 128/772 |
| 4,579,127 A | | 4/1986 | Haacke ....................... 128/772 |
| 4,634,042 A | | 1/1987 | Smith ...................... 228/173.4 |
| 4,651,513 A | * | 3/1987 | Dambre ....................... 57/217 |
| 4,654,477 A | | 3/1987 | Isoda ..................... 174/128 R |
| 4,679,387 A | * | 7/1987 | Weidenhaupt et al. ........ 57/212 |
| 4,682,607 A | | 7/1987 | Vaillancourt et al. ....... 128/772 |
| 4,689,444 A | | 8/1987 | Burgess .................. 174/128 R |
| 4,705,096 A | * | 11/1987 | Chia ........................... 164/476 |
| 4,731,134 A | * | 3/1988 | Alloin et al. ................. 156/53 |
| 4,759,806 A | * | 7/1988 | Dambre .................... 148/12 B |
| 4,763,466 A | * | 8/1988 | Abe et al. ...................... 57/213 |
| 4,777,324 A | | 10/1988 | Lee ............................ 174/34 |
| 4,778,246 A | * | 10/1988 | Carroll .................... 350/96.23 |
| 4,843,696 A | * | 7/1989 | Gentry et al. ............... 29/33 F |
| 4,922,924 A | | 5/1990 | Gambale .................... 128/772 |
| 4,925,445 A | | 5/1990 | Sakamoto et al. ............ 604/95 |
| 5,018,993 A | * | 5/1991 | Durham ...................... 439/801 |
| 5,069,217 A | | 12/1991 | Flesichhacker ............. 128/657 |
| 5,074,140 A | * | 12/1991 | Sanders ........................ 72/248 |
| 5,129,890 A | | 7/1992 | Bates et al. .................. 604/281 |
| 5,133,121 A | * | 7/1992 | Birbeck et al. ............... 29/872 |
| 5,147,662 A | * | 9/1992 | Nishijima et al. ........... 425/500 |
| 5,167,399 A | * | 12/1992 | Delomel ............... 254/134.3 R |
| 5,190,546 A | * | 3/1993 | Jervis ........................... 606/78 |
| 5,211,772 A | | 5/1993 | Ashida et al. ............... 148/336 |
| 5,213,111 A | | 5/1993 | Cook et al. .................. 128/772 |
| 5,215,246 A | | 6/1993 | Thompson et al. .......... 228/171 |
| 5,217,026 A | | 6/1993 | Stoy et al. ................... 128/772 |
| 5,240,520 A | | 8/1993 | Tarui et al. .................. 148/532 |
| 5,242,759 A | | 9/1993 | Hall ............................ 428/610 |
| H1239 H | | 10/1993 | Dusek .......................... 264/63 |
| 5,251,640 A | | 10/1993 | Osborne ..................... 128/772 |
| 5,260,516 A | | 11/1993 | Blackmore ............... 174/113 A |
| 5,310,574 A | * | 5/1994 | Holtmann .................... 427/58 |
| 5,317,804 A | * | 6/1994 | Kasper ........................ 29/860 |
| 5,322,508 A | | 6/1994 | Viera ........................... 604/52 |
| 5,333,620 A | | 8/1994 | Moutafis et al. ............ 128/772 |
| 5,334,166 A | | 8/1994 | Palestrant ................... 604/265 |
| 5,343,934 A | | 9/1994 | Wilson ........................ 164/476 |
| 5,368,661 A | | 11/1994 | Nakamura et al. .......... 148/512 |
| 5,417,690 A | | 5/1995 | Sennett ........................ 606/61 |
| 5,418,331 A | * | 5/1995 | Delalle ........................ 174/87 |
| 5,418,333 A | | 5/1995 | Sanders ...................... 174/129 |
| 5,429,139 A | | 7/1995 | Sauter ........................ 128/772 |
| 5,433,200 A | | 7/1995 | Flesichhacker ............. 128/657 |
| 5,437,288 A | | 8/1995 | Schwartz et al. ............ 128/772 |
| 5,437,748 A | | 8/1995 | Bhagwat et al. ............ 148/532 |
| 5,439,000 A | | 8/1995 | Gunderson ................. 128/664 |
| 5,451,718 A | | 9/1995 | Dixon ..................... 174/102 R |
| 5,476,211 A | * | 12/1995 | Khandros ................ 228/180.5 |
| 5,486,183 A | | 1/1996 | Middleman et al. ......... 606/127 |
| 5,515,603 A | * | 5/1996 | Ziemek et al. ................ 29/828 |
| 5,520,194 A | | 5/1996 | Miyata et al. .............. 128/772 |
| 5,535,612 A | | 7/1996 | Vijayakar ..................... 72/43 |
| 5,571,086 A | | 11/1996 | Kaplan et al. ................ 604/96 |
| 5,571,087 A | | 11/1996 | Ressemann ................. 604/96 |
| 5,571,094 A | | 11/1996 | Sirhan ........................ 604/284 |
| 5,588,443 A | | 12/1996 | Davidson .................... 128/772 |
| 5,597,378 A | | 1/1997 | Jervis ........................... 606/78 |
| 5,616,197 A | | 4/1997 | Helfer et al. ................ 152/527 |
| 5,632,746 A | | 5/1997 | Middleman et al. .......... 606/78 |
| 5,709,760 A | | 1/1998 | Prakash ....................... 152/556 |

\* cited by examiner

ELECTRICAL CONDUCTOR COILS AND METHODS OF MAKING SAME

This application is a continuation-in-part, of application Ser. No. 08/843,405 filed May 2, 1997 now U.S. Pat. No. 5,994,647, and a continuation-in-part of Ser. No. 08/963,686 filed Nov. 4, 1997, now U.S. Pat. No. 6,049,042, the complete disclosures of which are hereby incorporated by reference herein. This application is also related to copending Ser. No. 09/048,746, filed simultaneously herewith.

BACKGROUND OF THE INVENTION

1. Field of the Invention

The invention relates to electrical conductors. More particularly, the invention relates to electrical conductors which exhibit low resistance, spatial efficiency, low weight, good flexibility, enhanced bandwidth, minimized parasitic capacitance and inductance, and which are well suited for use, for example, in coils, solenoids, motors, and transformers.

2. State of the Art

Parent application Ser. No. 08/843,405 which is referenced above describes the general techniques known in the art for making electrical cables from helically twisted filaments, and proposes methods of twisting and drawing wire cables for enhancing the conductivity, flexibility and tensile strength of the cables. In addition to low resistance, flexibility and tensile strength, other characteristics of cables may be important depending on the application in which the cable is used. For example, the ability of a cable to remain cool during operation is often an important consideration. For cables used outdoors for power transmission, renitence to corrosion and low weight of the cable are important considerations. For cables which are subjected to repeated flexion, good flexibility as well as high fatigue strength are important. In cables which are used as leads for semiconductors and other electronic components, parasitic capacitance is an important consideration.

Parent application Ser. No. 08/963,686 which is referenced above discloses cables made from plated filaments which are first twisted together and then drawn through reducing dies (or swaged), filaments which are twisted together around a core material which melts or deforms during drawing of the cable through reducing dies, filaments which are twisted around a tube prior to drawing through reducing dies, and cables which are made from combinations of these methods. The cables exhibit a conductivity comparable to cables having greater diameter and weight. The smaller diameter of the cables of the invention allows them to be used as leads for electronic components in order to achieve reduced parasitic capacitance without increased resistivity or reactance or component package size. The cold working of the cables of the invention provides them with enhanced flexibility and fatigue strength. The combination of materials used in the cables of the invention provides them with renitence to corrosion and the adverse affects of aging as well as enhanced conductivity. Cables formed with a hollow tube core can be self-cooling, or easily cooled by flowing a coolant through the hollow core. The hollow tube core also enhances fatigue strength, resists the effects of aging, and lowers the weight of the cable. Cables formed with a silver core are also self-cooling.

Both of the parent applications recognize that multi-stranded electrical cable is generally more flexible than a single strand conductor which has similar conductive capacity. It is also recognized in the parent applications that multi-stranded cables have several disadvantages compared to single strand conductors. In particular, the parent applications teach that multi-stranded cables are spatially inefficient and possess self-induced parasitic inductance because of the helical paths of the strands which are not in perfect contact with each other. It is also recognized that the helical paths of the strands results in a longer conductive path (known as the "lay effect") and a corresponding increase in resistivity.

The physical properties of multi-stranded electrical cable also cause poor performance at very high frequencies (VHF) and ultra high frequencies (UHF). Signal losses at these frequencies are the result of multiple signal reflections along the length of a multi-stranded transmission line. Reflections occur where the cable exhibits an abrupt change in impedance due to the imperfect contact of the strands with each other. The reflected signals are typically out of phase with the transmitted signal and interfere destructively with the transmitted signal. This results in a "smearing" of signal pulses which limits the bandwidth of the transmission line.

The twisted and drawn multi-stranded wires of the parent applications maximize the spatial efficiency of a generally cylindrical conductor and achieve many other advantages as described above. However, there are certain applications where a generally cylindrical conductor is not the most spatially efficient. For example, where a conductor is wound to form a coil, a cylindrical cross-section is not necessarily the most spatially efficient.

The twisted and drawn multi-stranded wires of the parent applications also generally possess enhanced flexibility. However, certain electrical coils require relatively large diameter conductors wound to a relatively small radius. Winding a large diameter conductor to form a small diameter coil is difficult because the large diameter conductor may not have the flexibility to be wound so tightly. Use of a multi-strand conductor for such a coil introduces other problems regarding conductivity as described above. Moreover, it is usually desirable that the finished coil be inflexible. In addition, when a multi-strand conductor having a non-circular cross section is coiled, individual strands are pinched irregularly such that their cross sections change along their length. This change in cross sectional shape (even if cross sectional area remains the same) increases the resistivity of the conductor (known as the "pinch effect").

SUMMARY OF THE INVENTION

It is therefore an object of the invention to provide an electrical conductor which has low electrical resistance and which exhibits reduced parasitic capacitance and inductance.

It is also an object of the invention to provide an electrical conductor which has a structure which is spatially efficient.

It is another object of the invention to provide an electrical conductor which has a high bandwidth.

It is still another object of the invention to provide an electrical conductor which is well suited for use in coils, solenoids, motors, and transformers.

Yet another object of the invention is to provide methods of making electrical conductors and coils.

In accord with these objects which will be discussed in detail below, the electrical conductors of the present invention are made by twisting several strands together to form a flexible bundle, winding the bundle to form a coil (or other conductive structure), and fusing at least some of the strands to each other. Preferably, all or most of the strands are fused to each other.

According to one embodiment of the invention, conductive strands are coated with material which, when heated will fuse the strands to each other. The material used to coat the strands may be chosen from materials which form eutectic mixtures or eutectic alloys. Alternatively, the strands may be made from different materials which form eutectic mixtures.

According to a preferred embodiment, the twisted strands are drawn through one or more reducing dies to form an electrical conductor of reduced diameter having a substantially circular cross section. The conductor of reduced diameter having a substantially circular cross section is then preferably deformed by rolling with a plurality of rollers to form a conductor having a non-circular, e.g. rectangular cross section. These deformation steps precede the steps of winding and heating.

The conductors according to the invention have continuous, metallurgical bonding among the strands, reducing or eliminating the effects of helical conduction, while maintaining the flexibility of stranded wire during the manufacturing of coils or other formed conductors.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
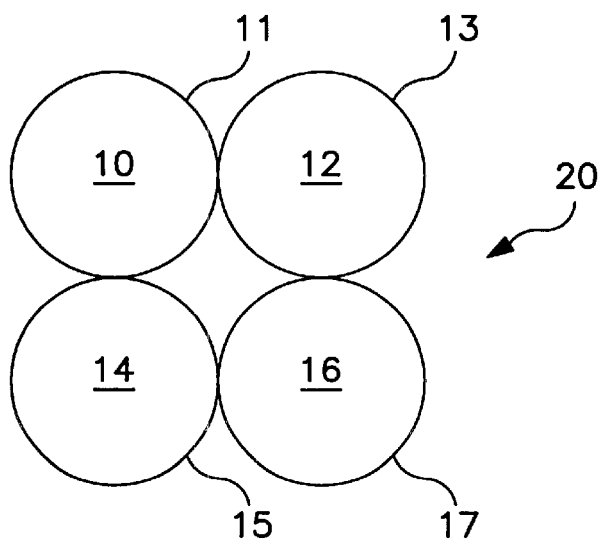
FIG. 1 is a schematic sectional view of a first embodiment of an electrical conductor according to the invention prior to forming and brazing.
Figure 2:
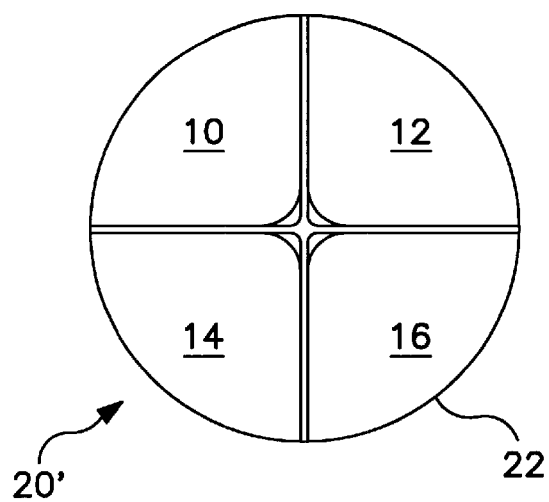
FIG. 2 is a schematic sectional view of the conductor of FIG. 1 after a first deforming operation.
Figure 3:
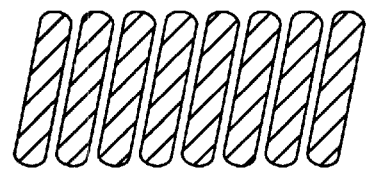
FIG. 3 is a schematic sectional view of the conductor of FIG. 2 after being wound into a coil prior to brazing.

Turning now to FIGS. 1–3, four 0.010" diameter copper wires 10, 12, 14, 16 are coated with a tin-lead eutectic alloy 11, 13, 15, 17 and are stranded together to form a flexible stranded conductor 20. The conductor 20 is drawn through one or more reducing dies to reduce its diameter to 0.014 inch. This compressing the strands 10, 12, 14, 16 forms a highly flexible conductor 20' with four sector-shaped strands and substantially no empty space as shown in FIG. 2. The highly flexible conductor 20' is preferably insulated with a high-temperature insulation 22, for example DuPont Pyre-ML. The insulated conductor 20', because it is highly flexible, may be tightly wound to form a coil structure 20" as shown in FIG. 3. Once the winding is completed, the coil is subjected to a baking treatment at a temperature (e.g., 400° F.) high enough to melt the conductive coating 11, 13, 15, 17 but not high enough to adversely affect the insulation 22 or the copper wire conductors 10, 12, 14, 16, 18.

According to the invention, the drawing of the conductor 20 to form the conductor 20' is preferably accomplished without the use of a lubricant which might interfere with the subsequent brazing step.

In this first example, all strands are coated with the meltable alloy. It will be appreciated, however, that it may be sufficient to coat only some of the strands. For example, only the two alternate strands 11 and 17 or 13 and 15 need to be coated in order to assure that all conductor interfaces are brazed together.

In order to ensure the wetting of the strands to each other, it may be advantageous to perform the baking operation in a reducing atmosphere (e.g., in the presence of dry hydrogen gas or "reforming gas" which is nitrogen plus hydrogen), in order to remove any oxides which may be present on the conductor strands. Alternatively, the strands may be coated with a thin coating of a non-activated or mildly-activated soldering flux, which does not require removal after brazing. The brazing operation may also be accomplished in an autoclave where additional contact pressure may be applied to improve bonding.

From the foregoing, it will be appreciated that the conductor 20' can be wound into a coiled structure 20" such as that shown in FIG. 3 while it is still very flexible, then converted to a more rigid conductor without the losses in efficiency caused by the lay effect and the pinch effect. According to the invention, the multiply-stranded compressed conductor 20' is produced as described above with conductive coatings on at least some of the strands which can be melted after the conductor has been bent into its final shape. The brazing according to the invention converts the flexible stranded conductor into a more rigid substantially solid conductor. The resulting substantially solid conductor is the electrical equivalent to a solid conductor which could not be wound as tightly as the intermediate flexible conductor according to the invention.

Figure 4:
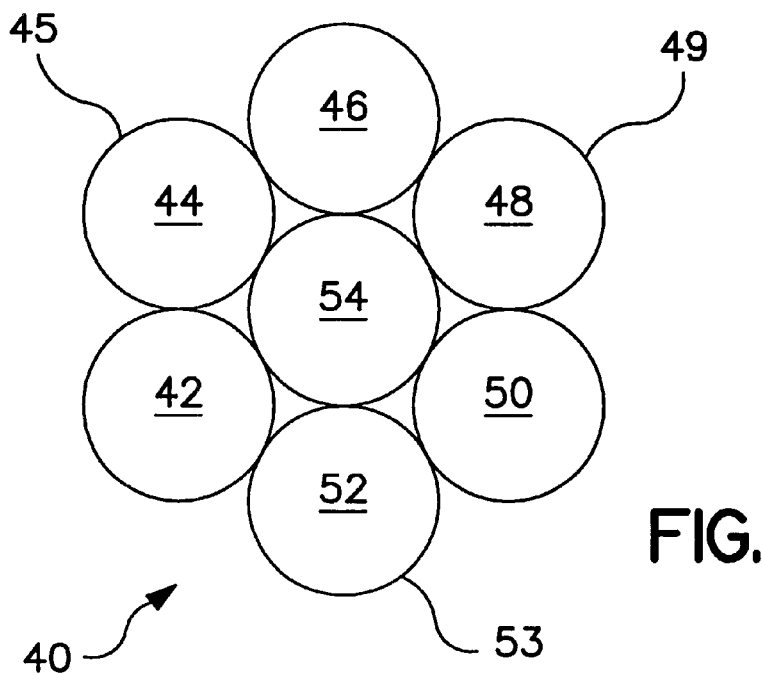
FIG. 4 is a schematic sectional view of a second embodiment of an electrical conductor according to the invention prior to forming and brazing.
Figure 5:
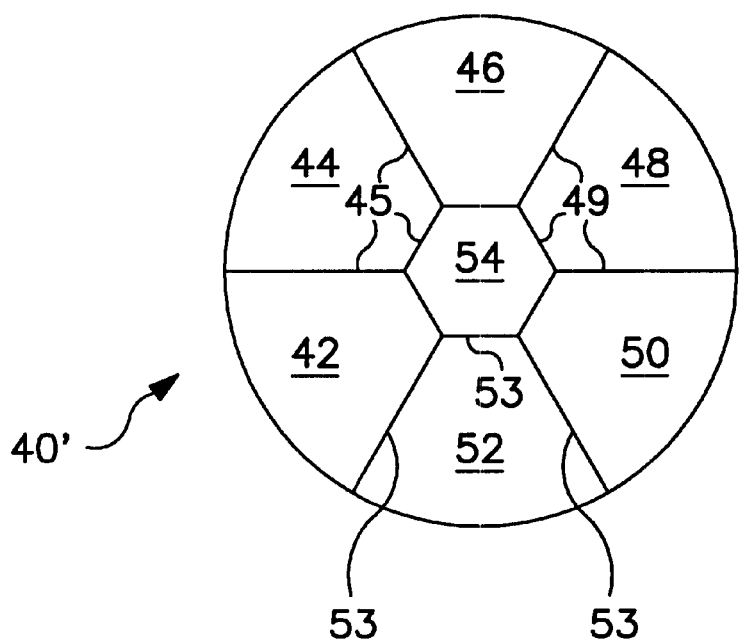
FIG. 5 is a schematic sectional view of the conductor of FIG. 4 after a first deforming operation.

With the foregoing principles in mind, those skilled in the art will appreciate that the stranded conductor may be formed in several different ways prior to drawing and brazing. Turning now to FIGS. 4 and 5, a conductor 40 according to the invention includes six outer conductors 42, 44, 46, 48, 50, 52 twisted around a central conductor 54. Each of the conductors has the same diameter, e.g. 0.010 inches. Three (44, 48, 52) of the six outer conductors are coated with a relatively lower melting temperature metal or metal alloy material 45, 49, 53. The conductor 40 is drawn through reducing dies as described above to form an extremely flexible conductor resembling conductor 40' in. FIG. 5 having a reduced diameter, e.g. 0.014 inches. It will be appreciated that the metal coating is now located between all of the strands with the possible exception of the center strand 54 and three outer strands 42, 46, 50. The flexible conductor 40' is wound to form a coil structure such as that shown in FIG. 3 and heated to melt the material 45, 49, 53. This brazing converts the flexible stranded conductor into a more rigid substantially solid conductor. The resulting substantially solid conductor is the electrical equivalent of a solid conductor which could not be wound as tightly as the intermediate flexible conductor according to the invention.

Figure 6:
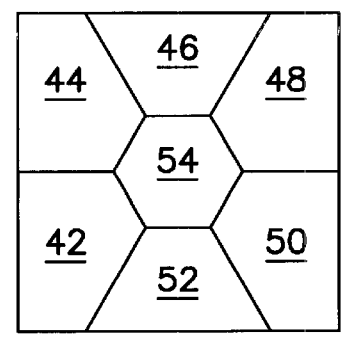
FIG. 6 is a schematic sectional view of the conductor of FIG. 4 after a second deforming operation.

According to another embodiment of the invention, it has been found to be desirable to shape conductors to a non-circular cross section for some applications. In particular, it is desirable when making coils that the wound conductor have a rectangular cross section rather than a circular cross section in order to achieve a high degree of spatial efficiency. Thus, according to the invention, a conductor such as the conductor 20' shown in FIG. 2 or 40' shown in FIG. 5 is mechanically deformed to produce the conductor which has a rectangular cross section similar to that of conductor 40" shown in FIG. 6. According to a presently preferred embodiment, the conductor 40" is first formed as the conductor 40', with the stranded wires being drawn to a compacted circular cross section as described above. The compacted conductor 40' is then further shaped to a different cross section as described below.

Figure 7:
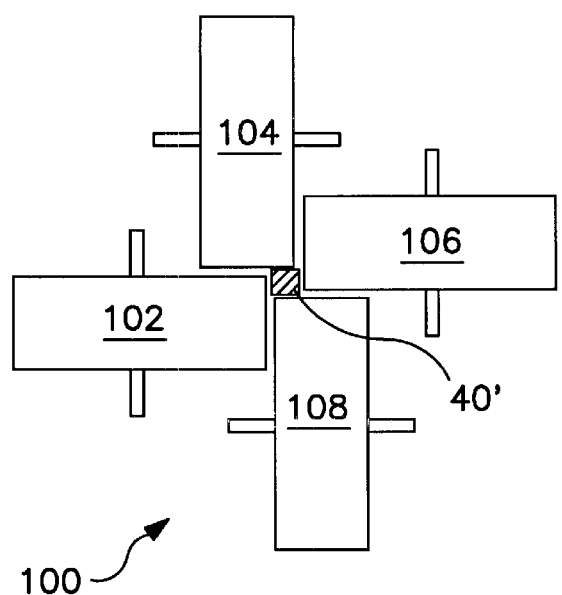
FIG. 7 is a schematic illustration of an apparatus used to form the conductor shown in FIG. 6.

One manner of deforming the conductor 40' is to use a rolling tool such as that shown schematically in FIG. 7. The tool 100 has four rollers 102, 104, 106, 108 which are arranged in an offset perpendicular manner relative to each other such that a central rectangular space is defined by the surfaces of the rollers. A wire or conductor such as the circular cross section conductor 40' is inserted into the central space defined by the rollers and the rollers are rotated as the wire is fed through the tool 100. Those skilled in the art will appreciate that the dimensions of the rectangular space defined by the rollers is readily altered by relocating the rotational axes of the rollers. According to a preferred embodiment of the invention, the conductor 40' is progressively rolled from its original circular cross section to a rectangular cross section. It is preferable to change the shape of the conductor in gradual steps, e.g. in increments of 10 to 20% until the wire is made substantially rectangular. The degree of compression per step is limited by the amount of compression that can be achieved without causing the multiple strands to become dislodged from each other, reducing the spatial efficiency of the wire, and resulting in unnecessary "pinching" of the wire in subsequent milling steps.

After the initial shape change, the now-rectangular (or square) wire is further reduced in cross-sectional area by further rolling steps. During these subsequent area-reduction steps it is appropriate to reduce the area in steps of approximately 20% per rolling step. It will be appreciated, however, that some metals which are difficult to roll, (such as severely work-hardened materials including cobalt alloys, stainless steels, chromium-copper alloys, precipitation-hardening copper alloys, etc.) need to be reduced by smaller increments. For a given material, once the maximum area reduction (which the material allows) has been achieved (for example, 90% for standard materials such as annealed copper or stainless steel) the wire must be annealed prior to further reduction. In practical operations, since it is easier and less expensive to reduce the area with round wire-drawing dies than with a complex roller arrangement, the wire is preferably first drawn to nearly the desired cross sectional area with round drawing dies, then subjected to the rolling apparatus to produce the square or rectangular shape with a relatively small amount of area reduction, perhaps 20%.

Those skilled in the art will appreciate that other roller arrangements may be used to produce conductors with different shaped cross sections. For example, an hexagonal shaped conductor can be formed with two rollers, each containing a trapezoidal groove. In all cases, however, it is preferable to arrange the rollers such that the wire is not pinched and no "fins" of material are extruded between rollers. If such fins are produced, they must be removed in a subsequent operation.

In all of the methods using multiple rollers, it has been found to be preferable to operate on the entire periphery of the wire at once along its length in order to produce shaped multiple-stranded wire. If, for example, the wire is first rolled between two rollers to flatten it, the strands of the wire may separate, and it may not be practical to then roll the wire with a second set of rollers at ninety degrees to form a square or rectangular wire.

It will also be appreciated that the conductors according to the invention may be shaped to a non-circular cross section by drawing round wire through shaped dies. Such dies are generally produced by combining multiple pieces of hard material (e.g., tungsten carbide or diamond) in the form of wedge-shaped sectors to form a converging die of the desired shape. It is also possible to produce such shaped dies directly by piercing a hard material such as diamond or carbide by means familiar to those in the art of die-making including inlet and exit tapers. Since such shaped dies result in reducing the wire in all directions at once, with substantially the entire periphery of the wire confined at a single point on its length, they may be used to produce shaped stranded wire from round, compressed, stranded wire.

Figure 8:
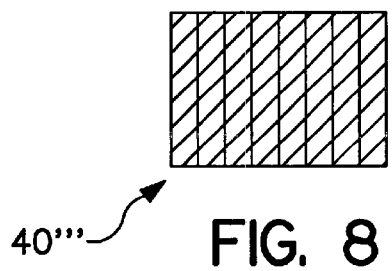
FIG. 8 is a schematic illustration of an electrical coil formed with the conductor of FIG. 6.

Referring now to FIG. 8, the conductor 40" is ideally suited for making a coil 40''' such as that shown in FIG. 8 which is extremely compact and spatially efficient. Preferably, the conductor 40" is wound to form a coil and heated to the melting point of the meltable coating material such that the strands are brazed to each other and the cooled coil exhibits a desirable rigidity and solidity.

From the foregoing, those skilled in the art will appreciate that the meltable coating material described herein may include many different conductive materials including lead, tin, a eutectic 63:37 tin:lead mixture, silver, a eutectic mixture of 2.7% silver and 97.5% tin, etc.

There have been described and illustrated herein several embodiments of an electrical conductor. While particular embodiments of the invention have been described, it is not intended that the invention be limited thereto, as it is intended that the invention be as broad in scope as the art will allow and that the specification be read likewise. Thus, while particular conductive meltable coatings have been disclosed, it will be appreciated that other coatings could be utilized. Similarly, while particular eutectic mixtures have been disclosed, other eutectic mixtures could be utilized. Also, while particular apparatus and methods have been shown for deforming the conductor to assume a circular or non-circular cross section, it will be recognized that other apparatus could be used with similar results obtained. Moreover, while particular configurations have been disclosed in reference to the number of strands in the conductor and the number of turns in the conductive coil, it will be appreciated that other configurations could be used as well. For example, conductors according to the invention amy be made from three, four, five, six, seven or more strands with or without a center or core strand. It will be appreciated that a conductor according to the invention, may include a central core which itself is made from a plurality of strands which are twisted and drawn. It will also be understood that although the examples given herein call for strands with the same diameter, it is possible to utilize aspects of the invention in conductors which are composed of strands having different diameters. Furthermore, while the conductors have been disclosed as having particular dimensions, it will be understood that different dimensions can achieve the same or similar function as disclosed herein. It will therefore be appreciated by those skilled in the art that yet other modifications could be made to the provided invention without deviating from its spirit and scope as so claimed.

What is claimed is:

1. A method of making an electrical conductor, comprising the steps of:

twisting a plurality of strands to form a bundle;

drawing the bundle through a die or swaging the bundle to form a conductive cable having a substantially circular cross section;

then winding the cable to form a coil; and then fusing at least some of the strands in the coil to each other with a conductive material.

2. The method according to claim 1, wherein:

said plurality of strands includes at least three strands; and each of the strands is fused to at least two other strands.

3. The method according to claim 1, wherein:

said step of fusing includes coating at least some of the strands with a meltable material and heating the coil.

4. The method according to claim 1, wherein:

said step of fusing includes coating at least some of the strands with a eutectic alloy and heating the coil.

5. The method according to claim 1, wherein:

said step of fusing includes choosing at least some of said strands to be made of materials which make a eutectic mixture when heated.

6. The method according to claim 1, further comprising:

covering the bundle with insulating material before winding.

7. The method according to claim 1, wherein:

said plurality of strands includes a center strand and a plurality of outer strands around said center strand, and said fusing comprises fusing each outer strand to at least said center strand and at least one other outer strand.

8. The method according to claim 1, wherein:

said plurality of strands includes a plurality of outer strands without a center strand.

* * * * *